(12) United States Patent
Brima et al.

(10) Patent No.: US 6,846,870 B2
(45) Date of Patent: Jan. 25, 2005

(54) HYDROTALCITES, SYNTHESES, AND USES

(75) Inventors: Thomas S. Brima, deceased, late of Pittsburgh, PA (US); by Gwendolyn Hawk, legal representative, Pittsburgh, PA (US); Masaki Fujii, Sewickley, PA (US); George R. Gallaher, Jr., Oakmont, PA (US); Sehyun Kim, Murrysville, PA (US); Edwin B. Townsend, IV, Pittsburgh, PA (US)

(73) Assignee: Sunoco, Inc. (R&M), Philadelphia, PA (US)

( * ) Notice: Subject to any disclaimer, the term of this patent is extended or adjusted under 35 U.S.C. 154(b) by 483 days.

(21) Appl. No.: 10/044,360

(22) Filed: Jan. 11, 2002

(65) Prior Publication Data

US 2003/0114699 A1 Jun. 19, 2003

Related U.S. Application Data

(63) Continuation-in-part of application No. 09/935,952, filed on Aug. 23, 2001.

(51) Int. Cl.$^7$ ............................. C08K 3/10; C08K 5/09; C07F 3/00
(52) U.S. Cl. ..................... 524/437; 524/394; 524/400; 524/504; 556/27; 556/71
(58) Field of Search ................................. 524/437, 394, 524/400, 504; 556/27, 71

(56) References Cited

U.S. PATENT DOCUMENTS

| | | | |
|---|---|---|---|
| 3,539,306 A | 11/1970 | Kumura et al. ............... 23/315 |
| 4,629,626 A | 12/1986 | Miyata et al. ............... 424/147 |
| 4,774,212 A | 9/1988 | Drezdon ...................... 502/62 |
| 5,064,804 A | 11/1991 | Soo et al. | |
| 5,177,138 A | 1/1993 | Moriyama et al. ........... 524/437 |
| 5,214,090 A | 5/1993 | Moriyama et al. ........... 524/424 |
| 5,216,058 A | 6/1993 | Visneski ...................... 524/357 |
| 5,280,065 A | 1/1994 | Moriyama et al. ............. 525/57 |
| 5,348,725 A | 9/1994 | Misra et al. ................. 423/594 |
| 5,399,329 A | 3/1995 | Schutz et al. | |
| 5,470,910 A | 11/1995 | Spanhel et al. ............. 524/785 |
| 5,507,980 A | 4/1996 | Kelkar et al. | |
| 5,518,704 A | 5/1996 | Kelkar et al. | |
| 5,578,286 A | 11/1996 | Martin et al. | |
| 5,595,747 A | 1/1997 | Kuroda et al. ............... 424/405 |
| 5,698,624 A | 12/1997 | Beall et al. .................. 524/445 |
| 5,728,364 A | 3/1998 | Martin et al. ............... 423/593 |
| 5,728,366 A | 3/1998 | Martin et al. | |
| 5,760,121 A | 6/1998 | Beall et al. .................. 524/450 |
| 5,844,032 A | 12/1998 | Serrano et al. ............. 524/445 |
| 5,849,830 A | 12/1998 | Tsipursky et al. ........... 523/450 |
| 5,877,248 A | 3/1999 | Beall et al. .................. 524/450 |
| 5,910,523 A | 6/1999 | Hudson | |
| 5,962,553 A | 10/1999 | Ellsworth ................... 523/216 |
| 5,973,053 A | 10/1999 | Usuki et al. | |
| 5,977,218 A * | 11/1999 | Bonora ......................... 524/91 |
| 6,313,208 B1 * | 11/2001 | Nosu et al. .................. 524/437 |
| 6,437,049 B1 * | 8/2002 | Bortolon et al. ............. 525/240 |

FOREIGN PATENT DOCUMENTS

| | | | |
|---|---|---|---|
| JP | 57 200433 A | 12/1982 |
| JP | 58 013643 A | 1/1983 |
| JP | 59 011308 A | 1/1984 |

OTHER PUBLICATIONS

Carlino S. "The intercalation of carboxylic acides into layered double hydroxides: a critical evaluation and review of the different methods," Solid State Ionics, North Holland Publishing Company, Amsterdam, NL, vol. 98, No. 1–2, Jun. 1, 1997, pp. 73–84.

Borja, M. et al. "Fatty Acids in Layered Metal Hydroxides: Membrane–Like Structures and Dynamics," Journal of Physical Chemistry, American Chemical Society, U.S., vol. 96, No. 13, 1992, pp. 5434–5444.

* cited by examiner

Primary Examiner—Tae H. Yoon
(74) Attorney, Agent, or Firm—Robert A. Koons, Jr.; Gary Mangels; Buchanan Ingersoll PC

(57) ABSTRACT

Synthetic hydrotalcites of the general formula

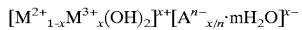

$$[M^{2+}_{1-x}M^{3+}_{x}(OH)_2]^{x+}[A^{n-}_{x/n} \cdot mH_2O]^{x-}$$

where $M^{2+}$ is a divalent cation, $M^{3+}$ is a trivalent cation and $A^{n-}$ is an organic anion selected from straight chain carboxylates of $C_{16}$–$C_{18}$ acids, carboxylates of aromatic acids, carboxylates of acrylic acid, unsaturated carboxylates of methacrylic acid, unsaturated carboxylates of vinylacetic acid and $C_2$ and higher organic acids containing heteroatoms such as nitrogen, phosphorous, sulfur and halogens are disclosed, along with methods of synthesis and uses.

26 Claims, 12 Drawing Sheets

HYDROTALCITES, SYNTHESES, AND USES

This application is a Continuation in Part of application Ser. No. 09/935,952, filed on Aug. 23, 2001.

FIELD OF THE INVENTION

This invention relates in general to novel synthetic hydrotalcites, their syntheses and uses. The synthetic hydrotalcites of the present invention can be made from organic anions longer than $C_4$, and also from organic anions with functional groups including saturated carboxylates of $C_6$, $C_8$, $C_{10}$, and $C_{18}$, straight chain acids; aromatics such as benzoates, chlorobenzoates, naphthoates, and p-hydroxybenzoates; carboxylates of acrylic, methacrylic, vinylacetic acids and mixtures of these organic anions. The synthetic hydrotalcites of the present invention can also be made from carboxylates of $C_2$ and higher organic acids containing heteroatoms such as nitrogen, sulfur, phosphorous and halogens.

BACKGROUND OF THE INVENTION

Hydrotalcites are derivatives of brucite, a naturally-occurring, layered, magnesium hydroxide mineral. Synthetic hydrotalcites can be made by substituting a trivalent metal cation, such as aluminum, for some of the magnesium cations normally present in a layer. The magnesium cations can also be substituted by other divalent cations. This substitution will result in a net positive charge residing on the layer, which requires an intercalating anion to achieve a net neutral charge for the molecule. The following general formula has been derived for synthetic hydrotalcites:

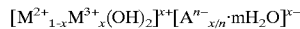

$$[M^{2+}_{1-x}M^{3+}_{x}(OH)_2]^{x+}[A^{n-}_{x/n} \cdot mH_2O]^{x-}$$

wherein $M^{2+}$ is magnesium and/or other divalent cation, $M^{3+}$ is aluminum and/or other trivalent cation and $A^{n-}$ is an anion. In addition to the anion, it will be noted that water is also a part of the lattice structure.

A group of hydrotalcites with a unique sheet-like morphology is described in U.S. Pat. No. 5,399,329, issued to Schutz, et al., and assigned to the assignee of the present invention. The entire contents of the Schutz '329 patent are incorporated herein by reference. The hydrotalcites of the Schutz '329 patent are comprised of anions derived from $C_1$ to $C_4$ saturated carboxylic acids. The general synthetic method of the Schutz '329 patent involves the reaction of an alumina source with a carboxylic acid in water followed by the reaction of the resulting mixture with a magnesium source. The approximate molar ratio of the reagents is as follows: 2 Mg:1 Al:1 anion; with the anion being the carboxylate of the acid used.

Although a hexagonal morphology is normally observed for non-carboxylate anion hydrotalcites, the carboxylate anion hydrotalcites of the Schutz '329 patent exhibit a unique morphology, termed therein "sheet-like". The distance between the hydrotalcite layers, as measured by d spacing, depends on the size of the intercalating anion. For example, carboxylate hydrotalcites from the following anions produced by the method of the Schutz '329 patent have a d spacing of: formate 7.64 Å, acetate 12.3 Å, propionate 13.02 Å, and isobutyrate 15.15 Å.

In the Schutz '329 patent, sheet-like hydrotalcites are prepared in aqueous medium by reacting alumina with a carboxylic acid at about 60° C. for 30 minutes followed by the addition of magnesium oxide at a temperature of 95° C. for about 6 hours. The desired gel hydrotalcite is obtained upon drying the reaction product. Although the method of the Schutz '329 patent works rather well for most water-soluble carboxylic acids such as $C_1$ to $C_4$ carboxylic acids, it does not work well for those acids, which are water-insoluble. In fact, butyric acid, which is a $C_4$ acid, has only limited success in the method of the Schutz '329 patent.

Hydrotalcites have many uses, including such applications as catalysts or catalyst precursors, ion exchangers, ion absorbers, ion-scavengers, and medical uses as antacids. Hydrotalcites are also used as nanocomposites in polymers to provide various property enhancements. Hybrid composites of polymer and other inorganic components such as clays and mica have been described in the prior art as having improved mechanical properties. The term nanocomposites reflects the dispersion of nano-scale particulates of the inorganic component of the hybrid in the polymer matrix.

In Japanese Patent Application 96-189168, assigned to Mitsui Petrochem Ind. Ltd., naturally-occurring hydrotalcites containing a carbonate anion are used in polypropylene synthesis, along with other additives, and are said to give good melt flow index, flexural modulus and Izod impact strength.

In EP 0,910,131, assigned to AtoChem, Fr., naturally-occurring hydrotalcites containing a carbonate anion are used in an ethylene-vinylacetate copolymer and are said to produce a film with good adhesion and barrier properties.

In Japanese Patent Application 86-296799, assigned to Du-Pont Mitsui Polychemicals Co., Ltd., naturally-occurring hydrotalcites containing a carbonate anion are used in linear, low density polyethylene and are said to produce a film which has thermal insulating properties and good tensile strength.

Most nanocomposite polymer applications use pillared clays and/or naturally-occurring hydrotalcites. Compounded compositions of nylon-6 and 5% clay nanocomposits have been shown to exhibit a 40% higher tensile strength, 68% greater tensile modulus, 60% higher flexural strength and a 126% flexural modulus (See, Int'l. SAMLE Symp. Exhib. 1998, 43:1053–1066). Nanocomposites are believed to disperse in the polymer in one of the following two ways:

1) in a disorderly fashion, such as by intercalation; or
2) by exfoliation, in which the nanolayers are regularly spaced in the polymer. Exfoliation is believed to lead to improved polymer properties.

There are references in both the patent and scientific literature of various clays, which have been modified and combined with polar polymers such as polyamides to form nanocomposite materials.

However, the introduction of nanoparticles into nonpolar polymers such as polyolefins to form a nanocomposite is a much more difficult task due to incompatibility of the polar nano particles with the nonpolar polymer. This incompatibility often leads to non-uniform distribution of the inorganic component throughout the polymer, leading to less than optimum performance. Typically, this difficulty is overcome by combining the nonpolar polymer with a similar, but chemically modified polymer (e.g. polypropylene-g-MA), which contains polar functionality to act as a compatibilizer molecule. The polar functionality of the modified polypropylene is able to interact with the polar character of the nanoparticle, and the nonpolar portion of the modified polypropylene interacts with the polypropylene matrix. Presumably, the interaction between the two polar functionalities provides both exfoliation and compatiblization, thereby resulting in a nanocomposite with uniform distribution of the nanoparticles.

U.S. Pat. No. 5,973,053 describes a layered composite clay material wherein organic onium ions and primary and secondary organic "guest" molecules are introduced into the interlayer space to increase the interlayer distance. The introduction of the organic onium ion acts to increase the compatibility of the clay with polymer and facilitate the dispersion of the clay in the hybrid composite.

In "Factors Controlling Mechanical Properties of Clay Mineral/Polypropylene nanocomposites", *Journal of Materials Sciences* 35 (2000) 1045–1050, Oya et al describe intercalating a clay with a polar monomer, diacetone acrylamide and maleic acid modified polypropylene as a compatibilizer. This organo-clay was then mixed with conventional polypropylene to prepare a nanocomposite. In "Poly (propylene)/organo-clay nanocomposite formation: Influence of compatibilizer functionality and organo-clay modification", *Macromolecular Material Engineering* 275, 8–17 (2000), Reichert et al describe the use of alkyl amines as intercalating agents in silica clay with and without the use of maleic anhydride modified polypropylene.

A need exists in the art for new synthetic hydrotalcites made from organic anions longer than $C_4$ and also those with functional groups including saturated carboxylates of $C_6$, $C_8$, $C_{10}$ and $C_{18}$ straight chain acids; aromatics such as benzoates, chlorobenzoates, naphthoates, and p-hydroxybenzoates; carboxylates of acrylic, methacrylic and vinylacetic acids; and mixtures of these organic anions. Such new synthetic hydrotalcites can find among their uses, that as nanocomposites in polymer applications, because these synthetic hydrotalcites are customizable according to the properties desired in the polymers made therefrom. A need also exists for modified hydrotalcites made from carboxylates of $C_2$ and higher organic acids containing heteroatoms such as nitrogen, sulfur, phosphorous and halogens, which can be used in polymer nanocomposites and are more easily dispersed in a non-polar polymer without the necessity of using a compatibilizer.

SUMMARY OF THE INVENTION

The present invention provides a synthetic hydrotalcite of the general formula, $$[M^{2+}_{1-x}M^{3+}_x(OH)_2]^{x+}[A^{n-}_{x/n} \cdot mH_2O]^{x-}$$

wherein $M^{2+}$ is a divalent cation, $M^{3+}$ is a trivalent cation and $A^{n-}$ is an organic anion selected from straight chain carboxylates of $C_5$–$C_{18}$ acids, carboxylates of aromatic acids, carboxylates of acrylic acid, unsaturated carboxylates of methacrylic acid and unsaturated carboxylates of vinylacetic acid.

The present invention also provides a synthetic hydrotalcite of the general formula $$[M^{2+}_{1-x}M^{3+}_x(OH)_2]^{x+}[A^{n-}_{x/n} \cdot mH_2O]^{x-}$$

wherein $M^{2+}$ is a divalent cation, $M^{3+}$ is a trivalent cation and $A^{n-}$ is an anion comprising a mixture of at least two members of the group consisting of straight chain saturated carboxylates of $C_2$–$C_4$ acids, carboxylates of aromatic acids, carboxylates of acrylic acid, unsaturated carboxylates of methacrylic acid and unsaturated carboxylates of vinylacetic acid.

The present invention also provides a synthetic hydrotalcite of the general formula $$[M^{2+}_{1-x}M^{3+}_x(OH)_2]^{x+}[A^{n-}_{x/n} \cdot mH_2O]^{x-}$$

wherein $M^{2+}$ is a divalent cation, $M^{3+}$ is a trivalent cation and $A^{n-}$ is an organic anion comprising a carboxylate of a $C_2$ or higher acid containing a heteroatom such as nitrogen, sulfur, phosphorous or a halogen. According to one embodiment, the heteroatom is nitrogen in the form of an amino acid. In this embodiment, the acid end of the amino acid binds to cation sites on platelets of the hydrotalcite leaving the amine end to interact or react with solvents or polymer molecules. Additionally, where a polymer is modified with an acid, such as in maleated polypropylene, the amine is free to react with the acid moiety in the polymer to form an amide or imide. In this way, the synthetic hydrotalcite may be directly bonded to the polymer. Preferably, the amino acid is a straight chain alkyl. More preferably, the amino acid intercalated hydrotalcite is capable of self and/or reversible exfoliation. Even more preferably the amino-acid is 4-aminobutyric or 6-aminocaproic acid. Modified hydrotalcites, or organo-hydrotalcites according to the current invention can be used to for polymer nanocomposites, and do not necessarily require the use of compatibilizers to effect dispersion of the hydrotalcite through the polymer. In the embodiment where the synthetic hydrotalcite is capable of self exfoliation in a solvent, it may be maintained as a colloidal suspension after synthesis rather than being collected and dried.

The present invention further provides for a method of making a synthetic hydrotalcite of the general formula, $$[M^{2+}_{1-x}M^{3+}_x(OH)_2]^{x+}[A^{n-}_{x/n} \cdot mH_2O]^{x-}$$

wherein $M^{2+}$ is a divalent cation source, $M^{3+}$ is a trivalent cation source and $A^{n-}$ is an organic anion source selected from straight chain carboxylates of $C_5$–$C_{18}$ acids, carboxylates of aromatic acids, carboxylates of acrylic acid, unsaturated carboxylates of methacrylic acid, unsaturated carboxylates of vinylacetic acid and carboxylates of $C_2$ and higher acids containing heteroatoms such as nitrogen, phosphorous, sulfur and halogens, the method comprising: reacting the trivalent cation source with the organic anion source to produce an intermediate and reacting the intermediate with the divalent cation source to produce the synthetic hydrotalcite.

The present invention still further provides for a synthetic hydrotalcite polymer blend comprising a poly-addition polymer and a synthetic hydrotalcite of the general formula, $$[M^{2+}_{1-x}M^{3+}_x(OH)_2]^{x+}[A^{n-}_{x/n} \cdot mH_2O]^{x-}$$

wherein $M^{2+}$ is a divalent cation, $M^{3+}$ is a trivalent cation and $A^{n-}$ is an organic anion selected from straight chain carboxylates of $C_5$–$C_{18}$ acids, carboxylates of aromatic acids, carboxylates of acrylic acid, unsaturated carboxylates of methacrylic acid, unsaturated carboxylates of vinylacetic acid and carboxylates of $C_2$ and higher acids containing heteroatoms such as nitrogen, phosphorous, sulfur and halogens. In a preferred embodiment, the organic anion in the synthetic hydrotalcite is an amino acid. More preferably, the amino acid is one that promotes self and/or reversible exfoliation of the synthetic hydrotalcite. Additionally, the polymer may be modified or functionalized, such as with maleic acid. In the embodiment where the polymer is modified or functionalized with an acid, an amino acid intercalated hydrotalcite may be bonded to the polymer via an amide or imide formed by reaction of the amine function with the acid modified polymer.

The present invention yet further provides a method for making a synthetic hydrotalcite-polymer blend comprising: mixing an emulsion comprising a poly-addition polymer with a synthetic hydrotalcite of the general formula, $$[M^{2+}_{1-x}M^{3+}_x(OH)_2]^{x+}[A^{n-}_{x/n} \cdot mH_2O]^{x-}$$

wherein $M^{2+}$ is a divalent cation source, $M^{3+}$ is a trivalent cation source and $A^{n-}$ is an organic anion source selected from straight chain carboxylates of $C_5$–$C_{18}$ acids, carboxylates of aromatic acids, carboxylates of acrylic acid, unsaturated carboxylates of methacrylic acid and unsaturated carboxylates of vinylacetic acid, and carboxylates of $C_2$ and higher acids containing heteroatoms such as nitrogen, phosphorous, sulfur and halogens, to obtain the blend. In a preferred embodiment, the organic anion in the synthetic hydrotalcite is an amino acid. More preferably, the amino acid is one that promotes self and reversible exfoliation of the synthetic hydrotalcite. Additionally, the polymer may be modified or functionalized, such as with maleic acid. In the embodiment where the polymer is modified or functionalized with an acid, an amino acid intercalated hydrotalcite may be bonded to the polymer via an amide or imide formed by reaction of the amine function with the acid modified polymer.

BRIEF DESCRIPTION OF FIGURES

The present invention will be described for the purposes of illustration, but not limitation in conjunction with the following figures, wherein.

DETAILED DESCRIPTION OF INVENTION

Figure 1:
FIG. 1 is a micrograph of a synthetic hydrotalcite made in Example 1.
Figure 1:
Figure 1:
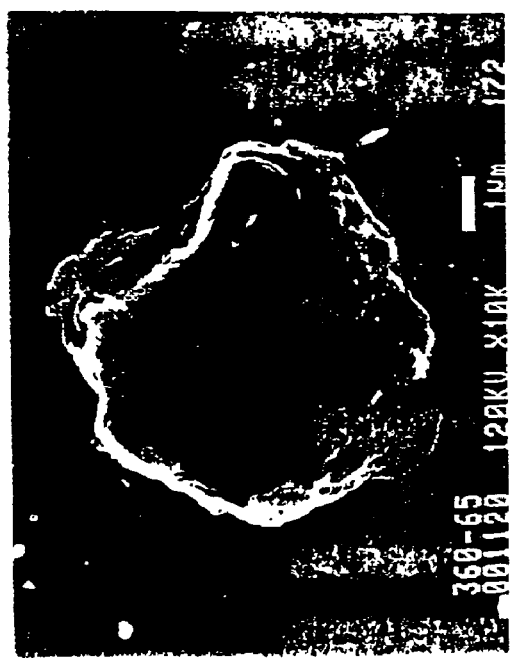

The three general steps of synthesizing hydrotalcites of the present invention are given below. Two alternate embodiments of Step III are provided.

Step I: Trivalent Cation Source+Organic Anion→Intermediate
60°–85° C., 4–8 hours Step II: Intermediate (in water)+Divalent Cation Source→Synthetic Hydrotalcite gel
90°–95° C., 4–8 hours Step III: Dry (evaporate/dry under vacuum, filter/dry under vacuum or spray-dry) or Step III: Maintain Wet (colloidal suspension/evaporate to concentrate or paste)

Success in preparing the synthetic hydrotalcites of the present invention depends greatly on the complete reaction in Step I, i.e., the trivalent cation reacting with the specific carboxylic acid. The preparation of hydrotalcites from longer chain than $C_4$ carboxylic acids, heteroatom containing acids and water-insoluble aromatic acids is accomplished by driving the reaction of Step I closer to completion preferably by utilizing one or more of the following approaches:

1) the reaction time for Step I can be increased from 30 minutes, as in the Schutz '329 patent, to from 4 to 8 hours;

2) inert organic solvents can be used as a reaction media for water insoluble-organic carboxylic acids with the trivalent cation source; and 3) Step I can be carried out in a melt of the organic anion.

In the examples described herein, the following materials were used: Trivalent cation source, unless otherwise specified was CATAPAL® alumina which is aluminum oxide monohydroxide from Vista Chemical Corporation; divalent cation source: Martin Magnesia Specialties Inc. MAGCHEM® 200D (a high purity, highly reactive magnesium oxide powder); acids were from Aldrich Chemical Company; and maleated polypropylene emulsion with non-ionic emulsifiers was from CHEMCOR containing 39–41% non-volatiles, Trade Name: POLY EMULSION 43N40® (used in the hydrotalcite-polypropylene blend preparation). For aminoacid intercalated hydrotalcite-polypropylene blend preparation, maleated polypropylene produced by Aristech, Trade Name: UNITE 1000®, was used.

The scanning electron microscopy (SEM) analyses of the synthetic hydrotalcite samples of the present invention were carried out by RJ Lee Group, Inc of Monroeville, Pa., USA. The analyses required collecting photomicrographs utilizing both secondary electron imaging (SEI) and transmission electron imaging (TED of typical particles in the samples. Three different typical particles from each sample were micrographed at magnifications ranging from 5,000× to 50,000× depending on the size of the particles.

Spray-Drying Method

Spray-drying of the synthetic hydrotalcites of the present invention can preferably be performed by using a Niro-2 fluid nozzle spray-dryer with the following settings: heat at 5.5, air pressure to the nozzle at 1 bar and the inlet temperature maintained at desired set range of 200–230° C. by varying the liquid feed rate (4–5 liters/hr). Water can preferably be fed to the spray-dryer after the temperature is stabilized to estimate the required feed rate and to remove any material remaining from a previous use.

Colloidal Suspension, Condensed Suspension or Paste

As an alternative to drying, the synthetic hydrotalcite may be maintained in a wet or moist state. Maintenance of the synthetic hydrotalcite in a wet or moist state is particularly desirable in embodiments of the invention where the synthetic hydrotalcite is capable or self exfoliation on contact with a solvent. In the case of a synthetic hydrotalcite that is capable of self exfoliation, the product can be isolated directly from the synthesis as a colloidal suspension of the exfoliated hydrotalcite and taken on without further processing. Alternatively, the suspension may be evaporated to form a concentrate of the suspension or a doughy paste.

Synthetic Hydrotalcite Preparation

As was mentioned previously, preparation of the synthetic hydrotalcites of the present invention is carried out in three steps. In Step I, the organic anion source is reacted with a trivalent cation source, preferably $Al^{3+}$, but as demonstrated in U.S. Pat. No. 5,518,704 incorporated herein in its entirety by reference, mixtures of $Al^{3+}$ and up to 50% of at least one of the other trivalent cations, $Cr^{3+}$ and $Fe^{3+}$, may also be used in synthetic hydrotalcite preparation. Step II is the reaction of the mixture from Step I with a divalent cation source, preferably $Mg^{2+}$, but as demonstrated in U.S. Pat. No. 5,518,704 incorporated herein in its entirety by reference, mixtures of $Mg^{2+}$ and at least one of the other divalent cations, $Ni^{2+}$, $Co^{2+}$, $Zn^{2+}$, $Cu^{2+}$, and $Mn^{2+}$, may also be used in synthetic hydrotalcite preparation. Step III is drying the resultant synthetic hydrotalcite. In alternative Step III, the hydrotalcite is maintained as a wet colloidal suspension, slurry or as a paste. Preferably, a synthetic hydrotalcite that is capable of self and/or reversible exfoliation is maintained in an exfoliated state as a slurry or paste. The Inventors have discovered that Step I of the preparation may be carried out in water, in an organic solvent, or in an acid melt, depending on the water solubility of the organic anion. Step II preferably is carried out in water.

By way of illustration and not limitation, preparations of a stearic acid synthetic hydrotalcite by methods utilizing each of the three approaches to improve Step I will now be described.

EXAMPLE 1

Step I Carried Out in Water Medium

CATAPAL® alumina (0.26 moles) was suspended in 500 ml deionized water in a 4-liter beaker and stearic acid (0.23 moles) was added to the stirred suspension. The beaker was fitted with a crystallizing dish filled with ice water to condense volatiles in the beaker as it was heated to 75°–85° C. and the temperature was maintained for 4 to 8 hours. At the end of this period, magnesium oxide (0.44 moles) was added, followed by 1.5 liters of deionized water. The mixture was heated to 90°–95° C. and the temperature was maintained for 4 to 8 hours. The mixture was cooled to room temperature overnight with stirring. The resulting material can preferably be dried in one of two ways:

a) in an air oven at 130° C. until a semi-dry solid is obtained, which is further dried in a vacuum oven at 80° C. overnight; or b) by spray-drying at approximately 200° C. inlet temperature and about 100° C. outlet temperature.

The powder obtained after drying the material is the intended synthetic hydrotalcite.

In water medium, a smaller than usual amount of water preferably is used, otherwise the acid may float above the alumina suspension in the water and slow the reaction rate. The product of this reaction was a greasy oil that was denser than the medium and settled to the bottom of the reaction vessel. In such a medium, some of the alumina and the free acid may be trapped and either reacts very slowly, or not at all, because mixing of the reagents becomes highly limited. The synthetic hydrotalcite made by this approach was not very homogenous as can be seen by reference to FIG. 1, which is a scanning electron micrograph of the sample.

EXAMPLE 2

Step I Carried Out in Organic Solvent(s)

Figure 2:
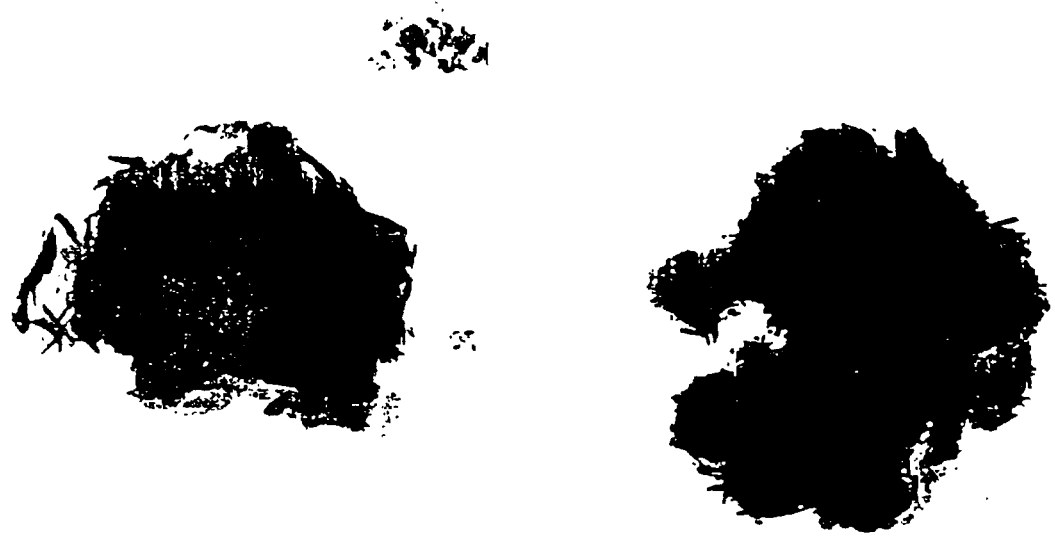
FIG. 2 is a micrograph of a synthetic hydrotalcite made in Example 2.
Figure 2:
Figure 2:

The reaction of the trivalent cation source and carboxylic acids that are water immiscible, such as stearic acid, can preferably be carried out in an organic solvent, such as refluxing hexane. CATAPAL® alumina (0.26 moles) was suspended in 200 ml hexane in a 4-liter beaker and the acid (0.23 moles) was added to the stirred suspension. The beaker was fitted with a crystallizing dish filled with ice water to condense volatiles in the beaker as it was heated to about 65° C. and the temperature was maintained for 4 to 8 hours. The solvent may preferably be removed by evaporation or filtration. Water was added to the resulting residue. Magnesium oxide (0.44 moles) was then added with vigorous stirring. The mixture was heated to about 90°–95° C. and the temperature was maintained for 4 to 8 hours. Product isolation, i.e., drying, was carried out as described in Example 1 above. Using this approach, a homogenous synthetic hydrotalcite was obtained with a larger d spacing value and with a seemingly smaller particle size as indicated by SEM, which can be seen by comparison of FIG. 1 to FIG. 2.

When Step I is carried out in an organic solvent, a faster, exothermic reaction occurs which results in an intermediate which is soluble in the medium. A disadvantage of this approach, however, is that the solvent preferably be removed before the reaction of the intermediate with the divalent cation source, because Step H is preferably carried out in water.

EXAMPLE 3

Step I Carried Out in an Acid Melt

A beaker containing the required amount of solid stearic acid was heated on an oil bath until the acid melted. The desired stoichiometric amount of alumina was added in small portions to the melt with stirring. The temperature was maintained for about two or more hours. Water was added to the product, and the mixture was stirred to an even consistency. Magnesium oxide was added, followed by 1.5 liters of deionized water. The mixture was heated to 90°–95° C. and the temperature was maintained for 4 to 8 hours. The mixture was allowed to cool to room temperature overnight with stirring. Product isolation was carried out as in Example 1 above.

A difficulty encountered with this approach was similar to that observed in Example 1, i.e., the product was greasy. However, an advantage of using the acid melt approach is that the reaction rate in an acid melt is much faster than that observed in water. With adequate mixing in the acid melt, a more complete reaction than that in water is expected. This may provide an economical approach in preparing synthetic hydrotalcites of solid fatty acids, which have moderate melting temperatures. The acid melt approach is faster than the water approach due to a faster reaction rate and it is faster than the organic solvent approach because there is no need to remove an organic solvent before proceeding to Step II. Table I summarizes the d spacing, the interlayer distance and the particle size of synthetic hydrotalcites made by each approach.

TABLE I

COMPARISON OF APPROACHES TO SYNTHESIZING STEARIC ACID HYDROTALCITE

| Example No. | Organic Anion Source | Step 1 Medium | d spacing Å | Interlayer Distance Å | Particle Size Microns |
|---|---|---|---|---|---|
| 1 | Stearic acid | Water | 19.4 | 14.6 | 11 × 6 |
| 2 | Stearic acid | Organic Solvent | 26.4 | 21.6 | 3 × 3 |
| 3 | Stearic acid | Acid melt | 24.4 | 19.6 | 5 × 3 |

EXAMPLES 4–20

Synthetic hydrotalcites from the following organic anion sources were prepared by methods of the present invention and some properties of these synthetic hydrotalcites are summarized in Table II: stearic acid; glycolic acid; acetic acid; acrylic acid; γ-butyrolactone; ethanesulfonic acid; lactic acid; hexanoic acid; octanoic acid; decanoic acid; benzoic acid; chlorobenzoic acid; cinnamic acid; naphthoic acid; methacrylic acid; acrylic acid, vinylacetic acid; a mixture of acrylic, acetic, and stearic acids; and a mixture of acetic, hexanoic, and stearic acids.

Figure 3:
FIG. 3 is a micrograph of a benzoic acid-derived synthetic hydrotalcite.
Figure 3:
Figure 3:
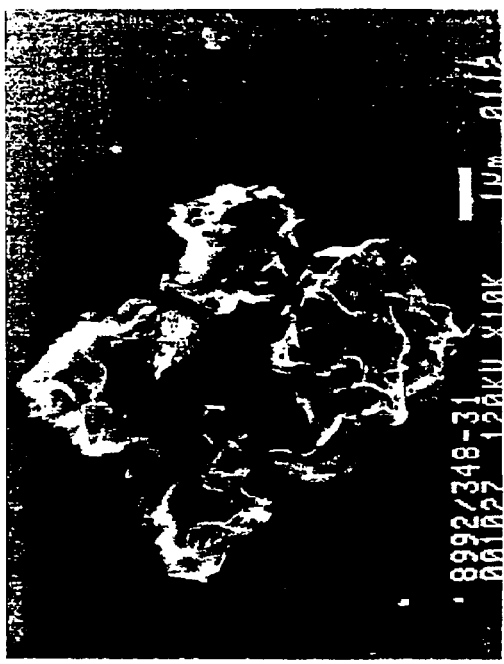
Figure 3:
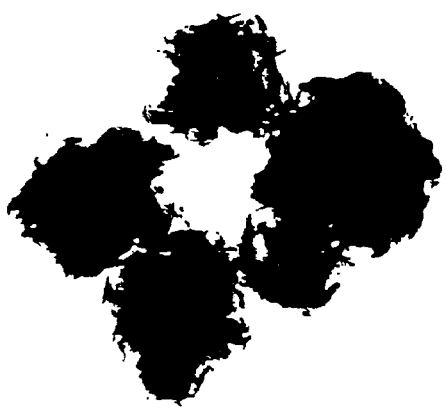
Figure 4:
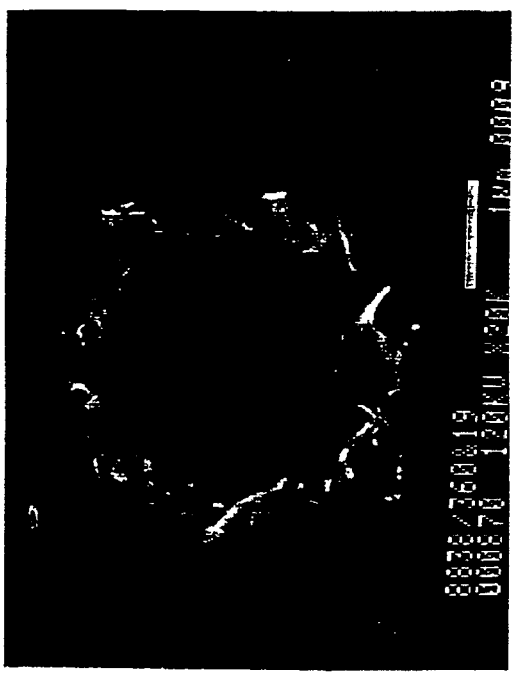
FIG. 4 is a micrograph of a methacrylic acid-derived synthetic hydrotalcite.
Figure 4:
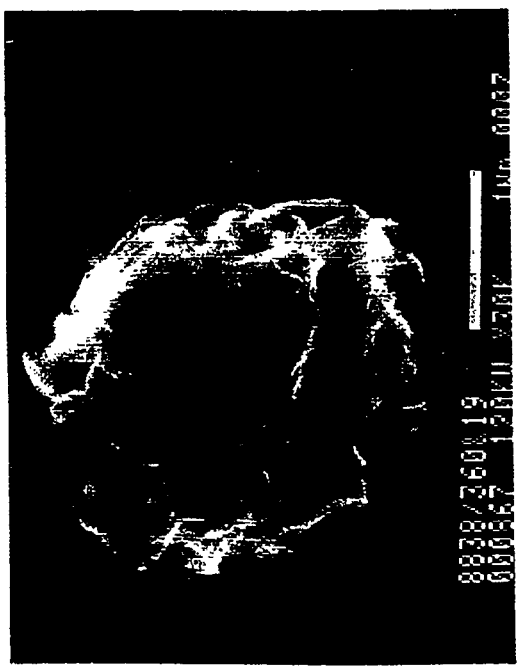
Figure 4:
Figure 4:
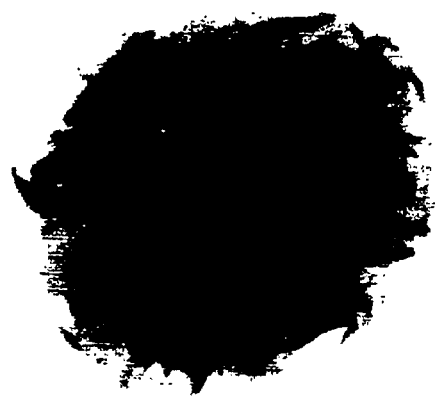
Figure 5:
FIG. 5 is a micrograph of an acrylic acid-derived synthetic hydrotalcite.
Figure 5:
Figure 5:
Figure 5:

With longer reaction times for Step I, synthetic hydrotalcites of the following organic anion sources can be prepared in water: ethanesulfonic acid, lactic acid, benzoic acid, methacrylic acid, acrylic acid, and vinylacetic acid. FIGS. 3–5 are scanning electron micrographs of three representative members of this group: benzoic acid, methacrylic acid, and acrylic acid, respectively.

All of the synthetic hydrotalcites described herein were analyzed by x-ray diffraction analysis (XRD) for the x-ray peak position, intensity and d spacing. The d-spacing is indicative of the distance between the layers in the hydrotalcite, because it is dependent upon the size and the shape of the anion in the hydrotalcite and is given for each of the synthetic hydrotalcites in Table II. The assumption that synthetic hydrotalcites with larger d spacing would mix with or exfoliate in polymers led to the synthesis of those hydrotalcites with larger anions or anions with longer carbon chains.

Figure 6:
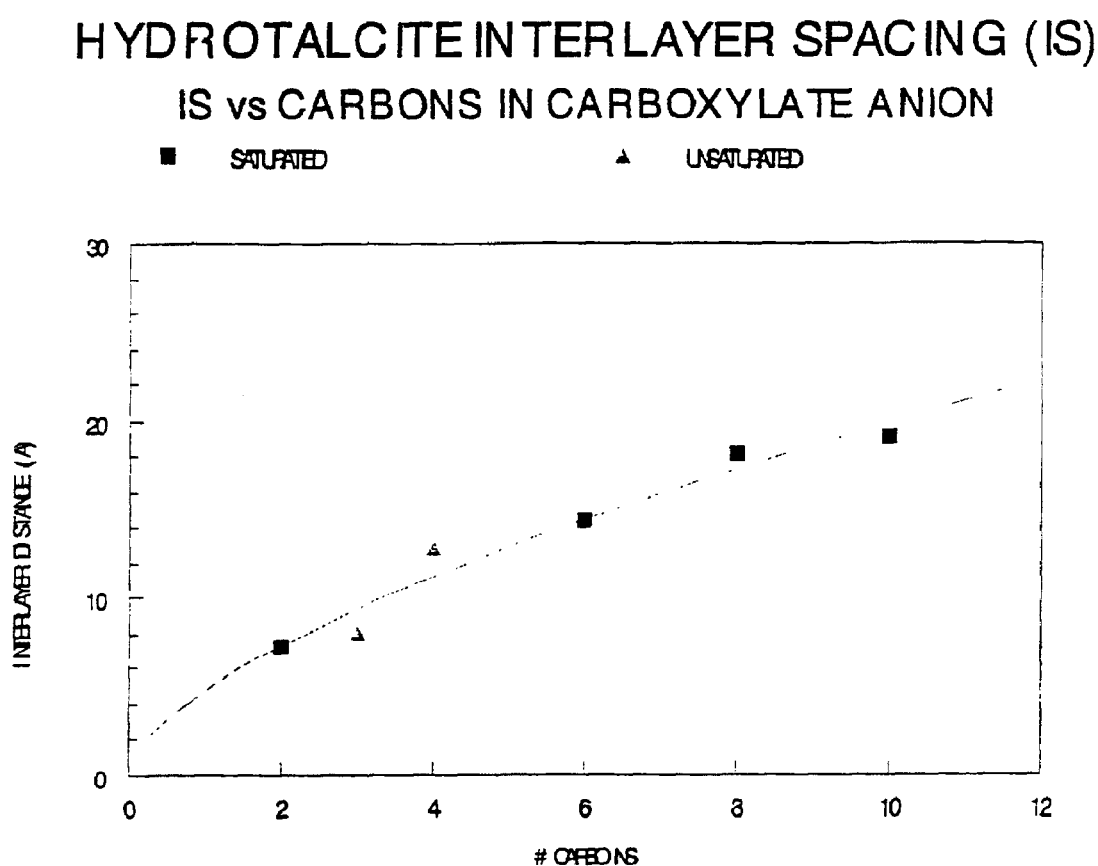
FIG. 6 illustrates the predicted relationship between interlayer distance and the number of carbon atoms in an anion.

FIG. 6 shows that as the number of carbon atoms in the anion increases, so does the hydrotalcite interlayer distance. This interlayer distance equals the d spacing minus the brucite layer thickness of 4.77 Å. In fact, there is a good correlation between the number of carbon atoms (at least up to $C_{10}$) in the organic anion and the interlayer distance. The highest interlayer distance obtained for the synthetic hydrotalcite made from stearic acid is 21.6 Å, which does not fit well in the prediction made from looking at FIG. 6. A predicted fit would be 26.0 Å, suggesting perhaps that beyond a certain number of carbon atoms there is enough flexibility in the carbon chain backbone to cause a deviation from the prediction.

Synthetic hydrotalcites which had a d spacing equal to or higher than 12 Å, the d spacing for acetic acid hydrotalcite, were subjected to SEM analysis to obtain the particle size, overall dimensions of the particles and the morphology for the synthetic hydrotalcite. As in the Schutz '329 patent, the preferred morphology for hydrotalcites of the present invention is sheet-like, herein termed "cabbage". Excellent examples of this morphology were obtained for the synthetic hydrotalcites prepared from the following anions: acetic, ethanesulfonic, octanoic, benzoic, chlorobenzoic, methacrylic, acrylic, and vinylacetic acids.

Figure 7:
FIG. 7 is a micrograph of a mixture of acetic, hexanoic, and stearic acids-derived synthetic hydrotalcite demonstrating a "semi cabbage" morphology.
Figure 7:
Figure 7:
Figure 7:

Other synthetic hydrotalcites which have a morphology herein described as "semi-cabbage" were those derived from the following anion sources: stearic acid, decanoic acid, naphthoic acid, mixed stearic, acrylic and acetic acids; mixed acetic, hexanoic and stearic acids, (See FIG. 7). "Semi-cabbage" as used herein means that only one or two of the three representative particles selected for micrography exhibited the cabbage morphology.

Without being limited to any specific theory, the Inventors believe that a possible explanation for this semi-cabbage morphology may be that the size and/or shape of the organic anion prevents it from conforming to the true cabbage formation within the crystal structure. Alternatively, the long carbon chain anion and the interlayer water molecules in the synthetic hydrotalcite structure may repel each other, thereby leading to a distortion in the crystal structure. It is also possible that an incomplete reaction with the trivalent cation in Step I of the hydrotalcite synthesis may lead to a semi-cabbage morphology.

Preparations carried out in water, which failed to result in synthetic hydrotalcites with the desired morphology, were from the following anion sources: glycolic acid, γ-butyrolactone and lactic acid. One possible explanation for the failure to produce synthetic hydrotalcites with the desired morphology from these water-soluble anion sources may be crosslinking between the layers due to the existence of double anions (carboxylate and hydroxylic) as indicated by solid state NMR.

The average size of the particles was measured in microns using the rulers shown in the SEM micrographs. A smaller particle size is preferred when the intended use for the synthetic hydrotalcite is in a nanocomposite. The particles of the synthetic hydrotalcites of the present invention are generally in the micron range as can be appreciated from a review of the data contained in Table II. The method of drying the synthetic hydrotalcites of the present invention did not seem to have any effect on the particle size.

COMPARATIVE EXAMPLES 22–24

Synthetic hydrotalcites made from a commercially available hydrotalcite (LaRoche, acetate anion HTC-0498-10), methacrylic, and acrylic acids with flash calcined alumina (FCA, available from LaRoche Industries) as the trivalent cation source gave a morphology that can, at best, be described as semi-cabbage. SEM indicated that more than one aluminum compound exists in FCA or that its reactivity with the acid is lower compared to CATAPAL® alumina. As can be appreciated from reference to Table II, the d spacing for HTC-0498-10 (Comparative Example 22) was 9.7 Å compared to 12.0 Å for a comparable synthetic hydrotalcite prepared in the assignee's laboratory from CATAPAL® alumina and acetic acid (Example 5).

TABLE II

SOME PROPERTIES OF SYNTHETIC HYDROTALCITES

| Example No. | Organic Anion Source | d spacing Å | Interlayer Distance Å | Particle Morphology | Particle Size microns |
|---|---|---|---|---|---|
| 1 | Stearic acid | 19.4 | 14.6 | semi-cabbage | 11 × 6 |
| 2 | Stearic acid[1] | 26.4 | 21.6 | semi-cabbage | 3 × 3 |
| 3 | Stearic acid[2] | 24.4 | 19.6 | Semi-cabbage | 5 × 3 |
| 4 | Glycolic acid | 9.2 | 4.4 | clump | 2 × 1 |
| 5 | Acetic acid | 12.0 | 7.2 | cabbage | 6 × 4 |
| 6 | γ-Butyrolactone | 12.3 | 7.5 | clump | 2 × 2 |
| 7 | Ethanesulfonic acid | 14.8 | 10.0 | cabbage | 6 × 3 |
| 8 | Lactic acid | 15.0 | 10.2 | Semi-cabbage | 3 × 4 |
| 9 | Hexanoic acid | 19.2 | 14.4 | clump | 5 × 3 |
| 10 | Octanoic acid | 22.9 | 18.1 | Semi-cabbage | 5 × 4 |
| 11 | Decanoic acid | 23.9 | 19.1 | Semi-cabbage | 4 × 3 |
| 12 | Benzoic acid | 17.0 | 12.2 | cabbage | 4 × 3 |
| 13 | Chlorobenzoic acid | 16.8 | 12.0 | cabbage | 3 × 4 |
| 14 | Cinnamic acid | 18.4 | 13.6 | clump | 7 × 4 |
| 15 | Naphthoic acid | 19.2 | 14.4 | Semi-cabbage | 6 × 6 |
| 16 | Methacrylic acid | 13.2 | 8.4 | cabbage | 6 × 5 |
| 17 | Acrylic acid | 16.6 | 11.8 | cabbage | 3 × 3 |
| 18 | Vinylacetic acid | 17.7 | 12.9 | cabbage | 6 × 4 |
| 19 | Mixed acids[3] | 15.5 | 10.7 | Semi-cabbage | 3 × 2 |
| 20 | Mixed acids[4] | 16.4 | 11.6 | Semi-cabbage | 6 × 3 |
| 21 | Octanoic acid | 20.3 | 15.5 | cabbage | 5 × 2 |
| Comp. Ex 22 | HTC-0498-10 | 9.7 | 4.9 | Semi-cabbage | 11 × 5 |
| Comp. Ex 23 | Methacrylic acid[5] | 14.0 | 9.2 | Semi-cabbage | 11 × 8 |
| Comp. Ex 24 | Acrylic acid' | 13.8 | 9.0 | Semi-cabbage | 7 × 5 |

[1]Step I of preparation was carried out in hexane solvent.
[2]Step I of preparation was carried out in stearic acid melt without a solvent.
[3]Mixture molar composition: 3.76 acrylic acid: 1.14 acetic acid: 0.57 stearic acid.
[4]Mixture molar composition: 1.34 acetic acid: 0.6 hexanoic acid: 0.8 stearic acid.
[5]Trivalent cation source was flash calcined alumina (FCA).

Solid CP-MAS $C^{13}$ NMR analyses of some of the hydrotalcites (Examples 1, 4, 6, 8, 12, 16, 17 and 18) indicated that in the majority of cases, the acids used in the preparations are indeed present in the carboxylate form. However, in a few instances (Examples 4, 6 and 8), a very small amount of the free acid is present with the corresponding anion, indicating an incomplete reaction in Step I.

EXAMPLE 25

Synthesis with 4-Aminobutyric Acid

Aluminum oxide monohydroxide (0.26 moles) was suspended in 50 ml deionized water in a 500 ml flask equipped with a reflux condenser and a stirrer, and 4-aminobutyric acid (0.26 moles) was added to the stirred suspension. The contents were heated to 75°–85° C. and the temperature was maintained for 4 to 8 hours. At the end of this period, magnesium oxide (0.52 moles) was added, followed by 150 ml of deionized water. The mixture was heated to 90°–95° C., and the temperature was maintained for 4 to 8 hours. The reflux condenser was removed to condense the content to the nominal solid concentration of 10% by weight. The mixture was then allowed to cooled to room temperature overnight with stirring. The resulting slurry was a stable viscous suspension, and the solid component did not precipitate.

An aliquot of the resulting slurry was placed in an air oven and at 130° C. until a semi-dry solid is obtained, which was further dried in a vacuum oven at 80° C. overnight. The powder obtained after drying the material was the intended synthetic hydrotalcite. A 0.5 g portion of the dry powder was placed in a test tube and re-wetted with 4.5 ml of water. The test tube was vigorously shaken for a minute and the slurry was allowed to stand one overnight. The slurry became a stable viscous suspension again, and the solid component did not precipitate.

EXAMPLE 26

Synthesis with 6-Aminocaproic Acid

The same procedure was repeated as in Example 25 except that 6-aminocaproic acid was used in place of 4-aminobutyric acid. The resulting slurry was a stable viscous suspension, and the solid component did not precipitate. The powder obtained after drying the material was the intended synthetic hydrotalcite. The re-wetted powder made a stable suspension again.

EXAMPLE 27

Synthesis with 4-Aminobenzoic Acid

The same procedure was repeated as in Examples 25 and 26 except that 4-aminobenzoic acid was used in place of 4-aminobutyric acid. The condensed slurry showed a quick precipitation into a powder layer and a clear supernatant layer. The powder obtained after drying the material was the intended synthetic hydrotalcite. The re-wetted powder did not make a stable suspension but separated into a precipitated powder layer and clear supernatant layer.

XRD of the HT samples were taken in the wet and dry state to determine if there was any difference in the basal peak. The data are shown in Table III. For 4-aminobutyric acid, the 2-theta peak observed at 5.70° (corresponding the interlayer spacing of 15.49 A) for the dry hydrotalcite is not observed in the wet sample, which indicates that the hydrotalcite is exfoliated in the wet state. Similar results are observed for 6-aminocaproic acid. This indicates that these organo hydrotalcites are self exfoliated on addition to a solvent. The data for 4-aminobenzoic acid indicate that this organo hydrotalcite is not self exfoliated on addition to a solvent.

TABLE III

SYNTHESIS OF ORGANO-HYDROTALCITES WITH AMINOACIDS

| Example No. | Organic Anion Source | d spacing dry Å | dry 2-theta | d spacing wet Å | wet 2-theta |
|---|---|---|---|---|---|
| 25 | 4-aminobutyric acid | 15.49 | 5.70° | exfoliated | non-existent |
| 26 | 6-aminocaproic acid | 14.02 | 6.30° | exfoliated | non-existent |
| 27 | 4-amino benzoic acid | 15.49 | 5.70° | 15.63 | 5.65° |

COMPARATIVE EXAMPLES 28–32

Preparation of Commercially Prepared Hydrotalcite-Polypropylene Blends

Two approaches were taken to prepare blends of commercially prepared hydrotalcite with CHEMCOR® polypropylene emulsion:

1) the dried hydrotalcite was regelled in water, mixed with the emulsion, and then spray-dried, or
2) the emulsion was added to the hydrotalcite before it was spray-dried to obtain the blend.

Blends with HTC-0498-10 (LaRoche) from 5% to 81% by weight in the solid weight of polypropylene were prepared as indicated in Table IV and analyzed by XRD, SEM, differential scanning calorimetry (DSC) and thermogravimetric analyses (TGA). Commercially prepared, HTC-0498-10 hydrotalcite had a limited regelling concentration of about 3% in warm water. This amount is much lower than the 8%–10% claimed by the manufacturer in its virgin gel before spray-drying. If this method of blend preparation were used, the low regelling concentration would require the use of large reactors.

TABLE IV

BLENDS OF COMMERCIALLY PREPARED HYDROTALCITE AND POLYPROPYLENE[1]

| Comparative Example No. | Weight Percent Hydrotalcite | d spacing Å | DSC Maxima, °C. | TGA Percent Residue |
|---|---|---|---|---|
| 28 | 5 | 6.3 | 147,380 | 9.6 |
| 29 | 9 | 6.2 | 147,374 | 10.2 |
| 30 | 34 | 6.2 | 151,329 | 22.4 |
| 31 | 38 | 6.2 | 151,328 | 23.5 |
| 32 | 61 | 11.4 | 149,331 | 46.1 |

[1]3% hydrotalcite HTC-0498-10 (LaRoche) was regelled in water at about 50° C. then polypropylene emulsion was added to the mixture.

The XRD analysis of the blends made from the commercially prepared hydrotalcite, HTC-0498-10, indicated a substantial decrease in d spacing from about 9.7 Å to 6.3 Å as the amount polypropylene became more than 60% as can be seen by reference to Table IV, but increased when the level was about 19%. Without being limited to any specific theory, the Inventors believe that a reason for this drop may be due to possible exfoliation or dispersion of the synthetic hydrotalcite in the polymer matrix.

Figure 8:
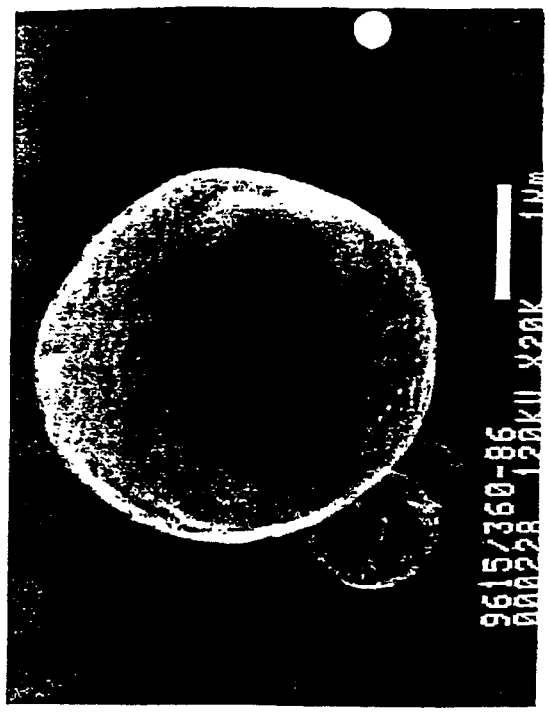
FIG. 8 is a micrograph of a blend of about 81% hydrotalcite with polypropylene demonstrating the preferred "cabbage morphology"
Figure 8:
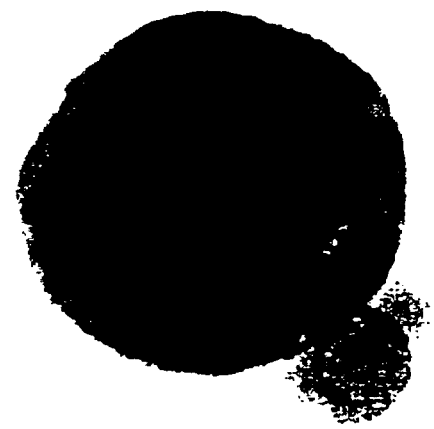
Figure 8:
Figure 8:
Figure 9:
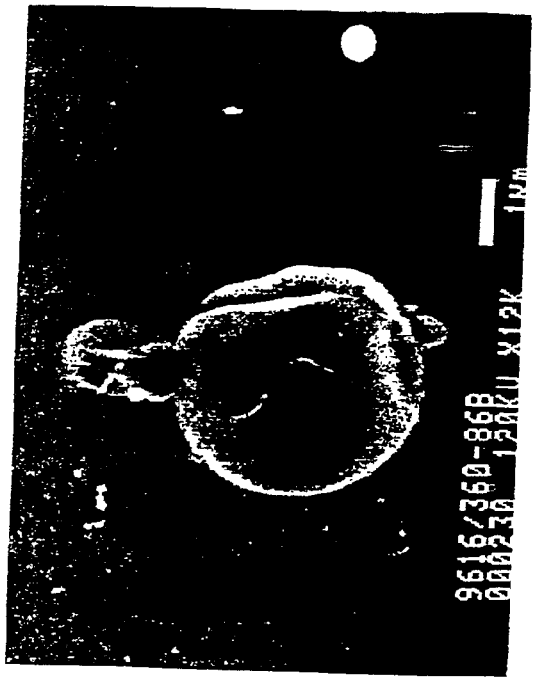
FIG. 9 is a micrograph of a blend of about 5% hydrotalcite with polypropylene demonstrating a "doughnut" morphology.
Figure 9:
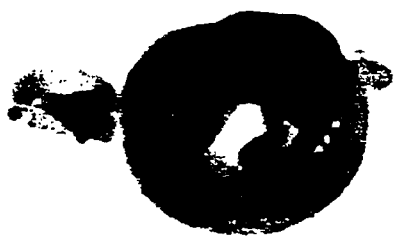
Figure 9:
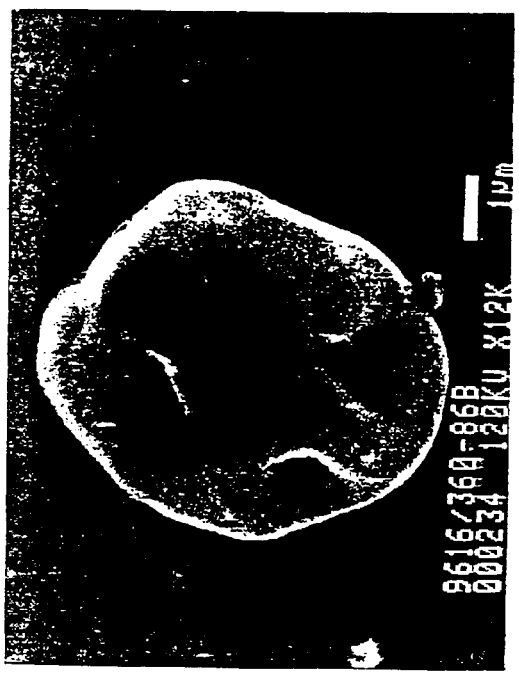
Figure 9:
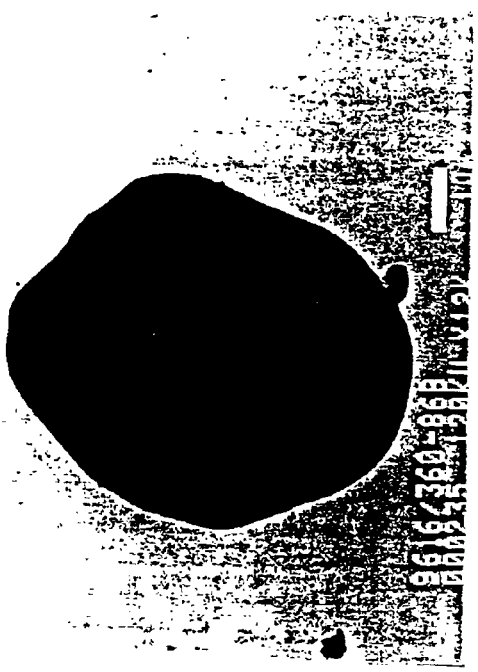

FIG. 8, a SEM micrograph of Example 32, a blend containing about 81% hydrotalcite, showed a cabbage morphology that was better defined than that of the hydrotalcite from which it was obtained. The SEM, shown in FIG. 9, of a similar blend with 5% hydrotalcite from Example 28, however, had a what the Inventors herein term a "doughnut" morphology. Without being limited to any specific theory, the Inventors believe that the doughnut morphology may result from the hydrophilic portion of the synthetic hydrotalcite forming a circular core while the hydrophobic portion, which comprises stearate or octanoate anion mixed with the polymer matrix, surrounds the circular core. The radii of the doughnut particles ranged from 2–3 microns. The blend of Example 28 may have the hydrotalcite so highly dispersed in the polymer matrix that it no longer exists in a layered form.

Thermogravimetric analyses of blends made from the commercially prepared hydrotalcite, HTC-0498-10, and polypropylene yield residue percentages that are indicative of the amount of hydrotalcite in the material. The residue percentages increased with the hydrotalcite percentage in the preparation as can be seen in Table V and represent non-volatile materials that remained after heating the sample to elevated temperatures.

The DSC transition temperatures represent the temperature at which phase changes take place in the blend and are indicative of minimum temperature required for processing these materials in polymer applications. The first phase transition temperature occurred at approximately 150° C. for the blends. Some of these materials exhibited lower transition temperatures that can be attributed to a loss of water.

EXAMPLES 33–38

Preparation of Synthetic Hydrotalcite-Polymer Blends

Preparation method 1 described above for Comparative Examples 28–32 was also used to prepare blends from some of the synthetic hydrotalcites of the present invention, namely those from stearic acid, octanoic acid, vinylacetic acid, and a mixture of acetic, hexanoic, and stearic acids. These synthetic hydrotalcites did not exhibit the regelling problem associated with the commercially prepared hydrotalcite, HTC-0498-10, which became very difficult to stir when the hydrotalcite concentration was above 3%. The second approach of adding the polypropylene emulsion as a final step in the preparation of hydrotalcite before spray-drying was also tested with synthetic hydrotalcites prepared from methacrylic and acrylic acids.

An amount of the synthetic hydrotalcite, which will result in about 3% weight, was added to water. The temperature of this mixture was raised to about 40° to 60° C. and the required amount of polypropylene emulsion, depending on desired blend composition, was slowly added to the gel with vigorous stirring. Enough water was added to keep the mixture fluid. The mixture was heated to about 80° C. and maintained at that temperature for about one hour and cooled overnight to room temperature with continued stirring. The mixture was spray-dried at an inlet temperature of 230° C. and an outlet temperature of 90°–105° C. Each blend was subjected to XRD, SEM, TGA and DSC analyses. The results from Examples 30–35 are summarized in Table V.

Synthetic hydrotalcite-polypropylene blends of stearic acid, octanoic acid, methyl methacrylic acid and acrylic acid were also prepared in a manner that required the addition of the polypropylene emulsion to the un-isolated synthetic hydrotalcite in the preparations. The resulting blend was isolated by spray-drying in the manner described above.

weight of the anion. The DSC transition temperatures for these materials were similar to those materials derived from HTC-0498-10, as the first transition temperatures ranged from 148°–152° C. These materials can therefore be processed with polymers at normal temperatures.

Although the method of blending the hydrotalcites of the present invention with poly-addition polymers is illustrated by the example of polypropylene, it will be readily apparent to those skilled in the art that other poly-addition polymers can be used in the present invention such as polyethylene,

TABLE V

SYNTHETIC HYDROTALCITE-POLYPROPYLENE BLENDS

| Example No. | Organic Anion Source | Percent Synthetic Hydrotalcite | Original d-spacing Å | d spacing Å | d spacing percent change | DSC Maxima, ° C. | TGA Percent Residue |
|---|---|---|---|---|---|---|---|
| 33 | Stearic acid[1] | 38 | 26.4 | 17.1 | −35.2 | 149 | 10.0 |
| 35 | Octanoic acid | 47 | 20.3 | 23.6 | +16.3 | 151 | 16.0 |
| 34 | Vinylacetic acid | 41 | 17.7 | 15.5 | −12.4 | 150 | 23.9 |
| 36 | Mixed acids[2] | 55 | 16.4 | 17.0 | +3.7 | 148 | 26.1 |
| 38 | Methacrylic acid[3] | 49 | 13.2 | 15.5 | +17.4 | 150 | 27.9 |
| 37 | Acrylic acid[3] | 57 | 16.6 | 13.7 | −17.5 | 152 | 37.2 |

[1]Stearic acid hydrotalcite made by method of example 2, i.e., in organic solvent.
[2]Mixed acids composed of the following molar ratio 1.34 acetic: 0.6 hexanoic: 0.8 stearic.
[3]Polypropylene emulsion was added to un-isolated synthetic hydrotalcite in the final mixture. All others were prepared by addition of previously isolated synthetic hydrotalcite that was regelled before polypropylene emulsion was added.

With the longer carbon chain synthetic hydrotalcites, the effect of the blend composition on the d spacings was mixed. As can be seen from a review of Table V, with blends of synthetic hydrotalcites of stearic acid, vinylacetic acid and acrylic acid there were drops in the d spacing of 35.2%, 12.4%, and 17.5% respectively, even at hydrotalcite compositions ranging from 38%–57%. For octanoic acid, mixed acids (acetic, hexanoic and stearic), and methacrylic acid, the d spacing for the blends increased respectively by 16.3%, 3.7%, and 17.4% compared to the synthetic hydrotalcites from which they were derived. Without being limited to any specific theory, the inventors believe that these results may suggest a lack of uniform blending of the synthetic hydrotalcites with the polypropylene or that the structures of the organic anions have a different influence on the d spacing in the blend. The SEM micrographs of blends of polypropylene with synthetic hydrotalcites prepared from octanoic and from mixed acids (acetic, hexanoic and stearic acids) exhibited a doughnut morphology.

Figure 10:
FIG. 10 is a micrograph of a blend of methacrylic acid-derived hydrotalcite with polypropylene.
Figure 10:
Figure 10:
Figure 10:
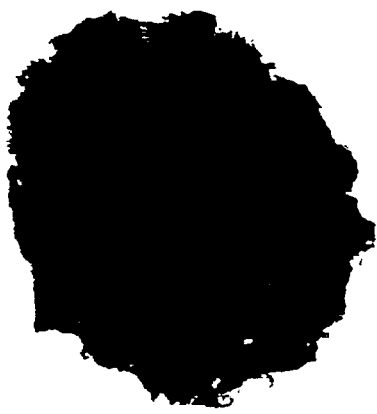

FIG. 10, which is a SEM micrograph of Example 34, a methacrylic acid-derived synthetic hydrotalcite polypropylene blend, did not exhibit the doughnut morphology, nor was it what could be referred to as semi-cabbage. The particle size of the methacrylic acid-derived synthetic hydrotalcite-polypropylene blend averaged 5×3 angstroms.

As seen in Table V, the residue percentages from TGA for the synthetic hydrotalcites made from anions other than acetate correlate with the hydrotalcite percentages in the blends when corrections are made for the contribution of the polybutene-1, poly-4-methyl-pentene-1, polystyrene and polyvinyl chloride.

EXAMPLES 39–41

Methyl Methacrylate Polymerization in the Presence of Synthetic Methacrylic Acid-Derived Hydrotalcite The reactions were carried in a 1-liter CHEMCO® reactor under 20 psig nitrogen at a stirring rate of 400 rpm. The amounts of methyl methacrylate, methacrylic acid-derived hydrotalcite and the reaction temperatures were as shown in Table VI. In each case, the reactor was charged with 460 ml water, 100 g methyl methacrylate and the desired amount of methacrylic acid-derived hydrotalcite. The reactor was first purged with nitrogen, then pressurized. 0.5 g AIBN (2,2-azobisisobutyronitrile) initiator and surfactant (Aerosol OT 75%, 2.5 g, available from Cytec Industries) were dissolved in 470 g methyl methacrylate and the solution was pumped (fed) at 88 ml/hr into the reactor which had been pre-heated to 70° C. The reaction continued until stirring became difficult due to the formation of solid product clumps. At that point, the methyl methacrylate feeding was stopped and the temperature was maintained for about 30 minutes to react any residual methyl methacrylate. After the reactor cooled to room temperature, polymer pieces were taken out and air-dried at room temperature, preferably in a fume hood. The amounts of polymer obtained are shown in Table VI.

TABLE VI

METHYL METHACRYLATE POLYMERIZATION IN THE PRESENCE OF
SYNTHETIC METHACRYLIC ACID DERIVED HYDROTALCITE

| Example No. | Methyl Methacrylate g | Methacrylic Acid-Derived Hydrotalcite g | Reaction temp. ° C. | Reaction Time hours | Polymer Produced g | DSC ° C., Maxima | TGA percent residue |
|---|---|---|---|---|---|---|---|
| 39 | 364 | 30 | 72–84 | 4 | 341 | 122,258 | 3.9 |
| 40 | 306 | 10 | 75–90 | 4 | 256 | 115,372 | 1.6 |
| 41 | 264 | 30 | 75–85 | 4 | 229 | 114,374 | 7.5 |

Co-polymerizing the synthetic hydrotalcite derived from methacrylic acid with methyl methacrylate demonstrates that master-batch materials may be prepared. Blends with poly-addition polymers, such as polypropylene, can then be prepared from these master batches. With the Aerosol OT surfactant, the copolymer was expected to be evenly slurried in the water in which the reaction was carried out. In all the examples, slurry formation occurred only at the beginning of the polymerization. As the polymer amount increased, the suspended particles coalesced into a ball or into chunks that forced the early termination of the polymerization because of difficulty with stirring. The product obtained was a tan, tough and stiff polymer.

TGA analyses of the products, as seen in Table VI, indicated varying levels of the methyl methacrylic acid-derived hydrotalcite (1.6% to 8%) based on the residue percentage. This percentage is indicative of the amount of alumina and magnesium left after all the carbon sources in the samples have been volatilized. The examples with highest starting weight percent of hydrotalcite yielded the highest residue percentage. The first DSC transition temperatures (114°–122° C.) were only small diffuse peaks and may not be indicative of the real polymer transition temperature. The second transition at 370° C. was likely due to the phase changes in the copolymer, this may indicate the need for higher processing temperatures in polymer applications. These polymers dissolved or formed a clear gel in toluene, ethyl acetate, and, to a limited extent, in methylene chloride. The copolymer with the least amount of synthetic methacrylic acid-derived hydrotalcite (1.6% residue by TGA) was the most soluble in toluene. When the solution containing this copolymer was dried, a clear film with good adhesive characteristics was obtained.

EXAMPLE 42

Compounding of Amino Acid Intercalated Hydrotalcite with Maleated Polypropylene Amino acid intercalated synthetic hydrotalcites according to the current invention are particularly useful for preparing inorganic polymer blends according to the current invention. In a preferred embodiment, the amino acid intercalated synthetic hydrotalcite is capable of self exfoliation when introduced into a solvent. Preferably, according to this embodiment, the amino acid intercalated synthetic hydrotalcite is maintained as a slurry, suspension or paste when it is isolated from the synthesis. In this embodiment, the amino acid intercalated hydrotalcite is isolated from the synthesis and is maintained in an exfoliated state. Alternatively, the amino acid intercalated synthetic hydrotalcite is dried after isolation and may be subsequently added to a solvent to induce self exfoliation. In either embodiment, the hydrotalcite is added to the molten polymer as a slurry, suspension or paste. Because the amino acid intercalated synthetic hydrotalcite is capable of self-exfoliation it can be more easily dispersed in a polymer blend without the use of a compatiblizer. Although a compatiblizer is not required, amino acid intercalated synthetic hydrotalcites according to this embodiment of the invention can be used with compatiblizer molecules.

In one embodiment, the amino acid intercalated synthetic hydrotalcite is compounded with a modified poly-addition polymer. Preferably, the modified poly-addition polymer is an acid modified polyolefin, such as maleated polypropylene. The hydrotalcite may be compounded with either the acid modified polymer alone or with a mixture of modified and unmodified polymers. According to one preferred embodiment, the amino acid intercalated synthetic hydrotalcite is compounded with a molten acid modified polyolefin, such as maleated polypropylene, to produce a "master batch" of amino acid intercalated synthetic hydrotalcite and acid modified polyolefin. This "master batch" may then be compounded with unmodified poly-addition polymers to produce a final nanocomposite.

While not wishing to be bound by theory, it is believed that the amine function of the amino acid intercalated hydrotalcite reacts with the acid moiety in the modified polyolefin to produce an amide or imide. In this way, the hydrotalcite is actually bound to the polymer, improving the dispersion of the hydrotalcite in the nanocomposite.

10 g of UNITE 1000® maleated polypropylene was added to 166.7 g of nominally 6 wt % (10.0 g) 6-aminocaproic acid-based hydrotalcite slurry in a 600 ml metal beaker in a heating jacket. Mixing was performed using a high speed (8000 rpm max) Gifford-Wood homomixer plugged into a variable transformer to allow adjustments to the mixing speed. The mixture was then heated while being stirred. Mixing/heating were continued until the mixture thickened into a thick, pasty material. This material was then removed from the beaker and allowed to air dry. A portion of this air-dried material was ground for XRD analysis.

XRD was performed on a ground sample of UNITE 1000® and the 50/50 UNITE/hydrotalcite mixed material, as well as on wet and air-dried hydrotalcite from a batch of hydrotalcite prepared in an 8 wt % slurry. The 6 wt % slurry is not viscous enough to perform XRD on in the wet state, so an 8 wt % preparation was used for this comparison. The 6 wt % and 8 wt % hydrotalcite slurries were prepared in the same manner, so no real difference would be expected between the two.

Figure 11:
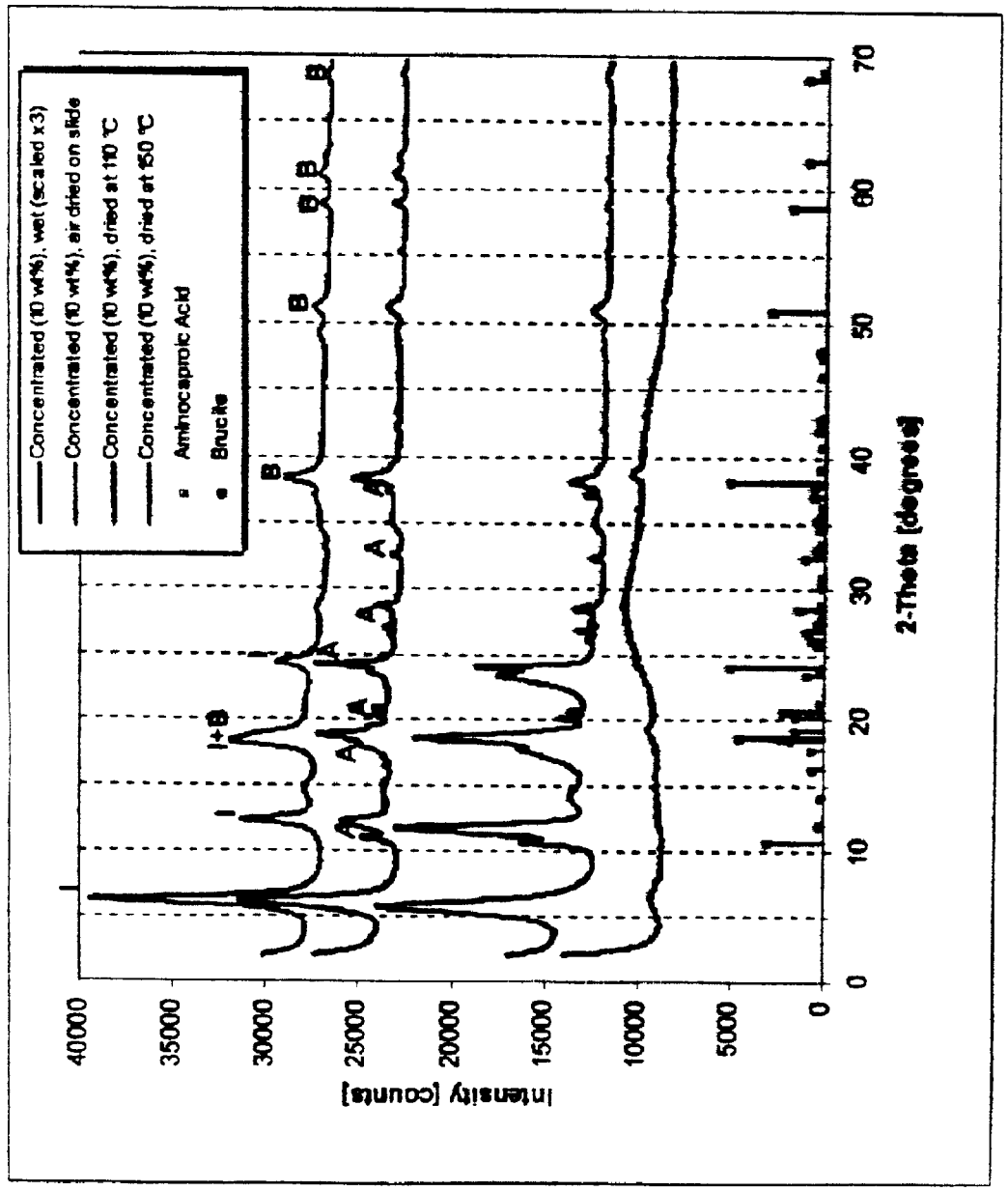
FIG. 11 shows XRD scans of an 8 wt % slurry of the hydrotalcite wet; an air-dried sample of hydrotalcite from an 8 wt % slurry; a sample of UNITE 1000®; and a sample of the 50/50 UNITE/hydrotalcite mix.

FIG. 11 shows from bottom to top XRD scans of an 8 wt % slurry of the hydrotalcite wet; an air-dried sample of hydrotalcite from an 8 wt % slurry; a sample of UNITE 1000®; and a sample of the 50/50 UNITE/hydrotalcite mix. Looking at FIG. 11, the region of interest in each scan is at approximately 6°. The scan for the air dried sample of the hydrotalcite (second from bottom) shows a strong basal peak in this region, indicative of the un-exfoliated state. The absence of this peak in the scan for the 8 wt % slurry (bottom) is indicative of the hydrotalcite being in the exfoliated state. Referring to the scan for the 50/50 UNITE/hydrotalcite mix (top), it can be seen that the basal peak is completely absent. The small peak that does appear is due to the UNITE 1000® resin.

Figure 12:
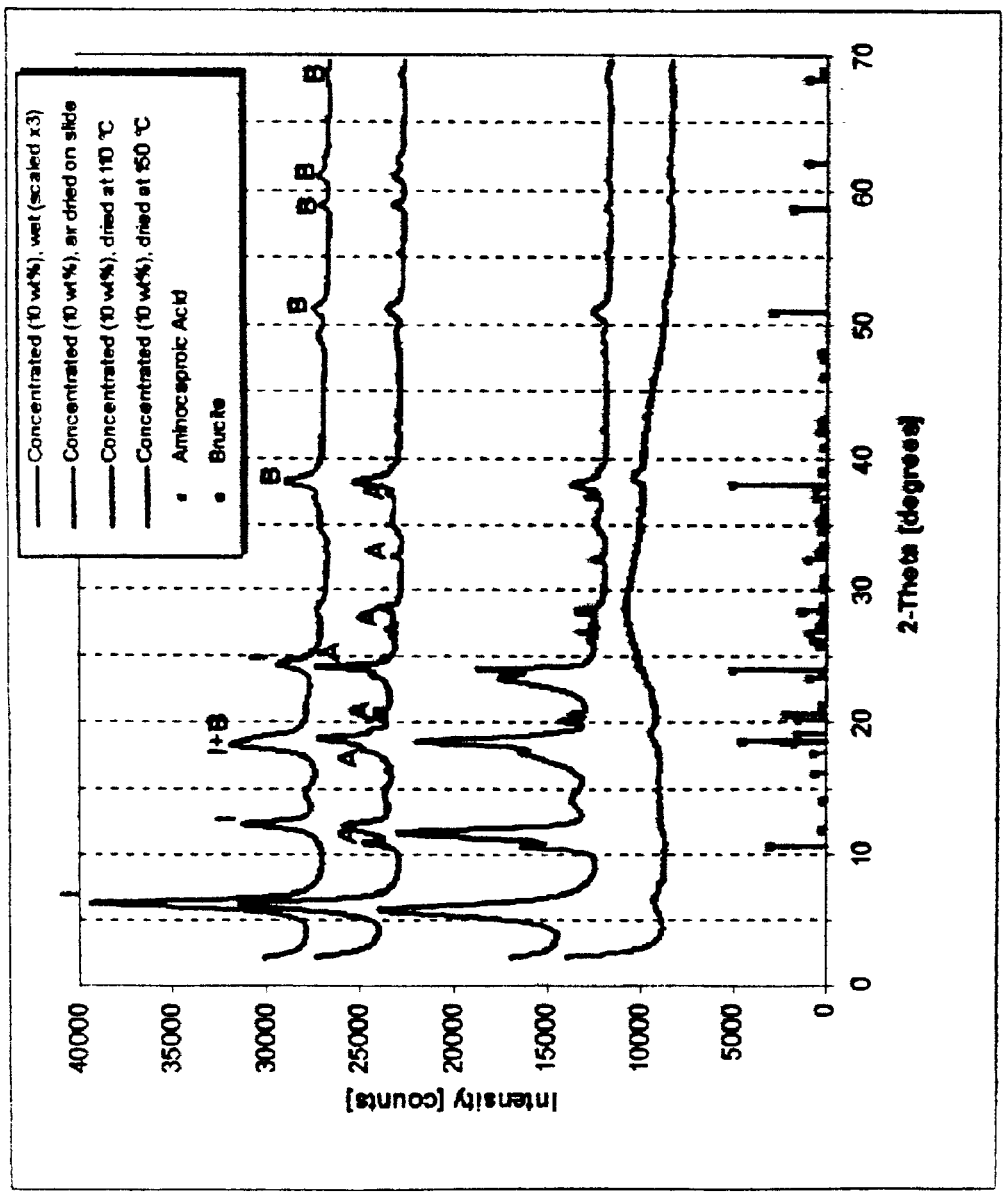
FIG. 12 shows XRD scans of a 10 wt % slurry of the hydrotalcite wet; an air-dried sample of hydrotalcite from an 10 wt % slurry; a sample of the 10 wt % slurry dried at 100° C. and a sample of the 10 wt % slurry dried at 150° C.

For comparison, FIG. 12 shows the evolution of the hydrotalcite structure from heating. FIG. 12 shows from bottom to top XRD scans of a 10 wt % slurry of the hydrotalcite wet; an air-dried sample of hydrotalcite from an 10 wt % slurry; a sample of the 10 wt % slurry dried at 100° C. and a sample of the 10 wt % slurry dried at 150° C. In the air dried sample (second from bottom), the peaks due to 6-aminocaproic acid appear in the region of about 12° to about 37°. Looking at the scans for the samples dried at 100° C. and 150° C. (second from top and top respectively) it can be seen that the peaks due to 6-aminocaproic acid eventually disappear with increasing heat treatment, leaving only peaks for the hydrotalcite structure (brucite layers+interlayer spacings) behind. Notably, the basal peak at approximately 6° continues to sharpen with increased heating until the hydrotalcite structure is destroyed.

Referring back to FIG. 11 it can be seen in the scan for the 50/50 UNITE/hydrotalcite mix (top), that the peaks indicative of 6-aminocaproic acid are still present. This indicates that the structure of the hydrotalcite was not destroyed in the preparation of the 50/50 mix. Further, the absence of the strong basal peak at approximately 6° indicates that the hydrotalcite is completely exfoliated. If the 50/50 UNITE/hydrotalcite mix was simply physical mixture of the polymer and un-exfoliated hydrotalcite the peak at approximately 6° would still be present. Thus, the 50/50 UNITE/hydrotalcite mix is a true nanocomposite.

The foregoing illustrations of embodiments of the present invention are offered for the purposes of illustration and not limitation. It will be readily apparent to those skilled in the art that the embodiments described herein may be modified or revised in various ways without departing from the spirit and scope of the invention. The scope of the invention is to be measured by the appended claims.

We claim:

1. A synthetic hydrotalcite of the general formula:

$$[M^{2+}_{1-x}M^{3+}_x(OH)_2]^{x+}[A^{n-}_{x/n} \cdot mH_2O]^{x-}$$

wherein $M^{2+}$ is a divalent cation, $M^{3+}$ is a trivalent cation and $A^{n-}$ is at least one organic anion comprising a carboxylate of an amino-acid.

2. The synthetic hydrotalcite of claim 1, wherein said divalent cation source, $M^{2+}$ consists essentially of $Mg^{2+}$.

3. The synthetic hydrotalcite of claim 1, wherein said trivalent cation source, $M^{3+}$ consists essentially of $Al^{3+}$.

4. The synthetic hydrotalcite of claim 1, wherein said amino acid comprises 4-aminobutyric acid.

5. The synthetic hydrotalcite of claim 1 wherein said amino acid comprises 6-aminocaproic acid.

6. The synthetic hydrotalcite of claim 1, wherein said hydrotalcite is capable of self exfoliation.

7. The synthetic hydrotalcite of claim 6, wherein said hydrotalcite is capable of reversible exfoliation.

8. The synthetic hydrotalcite of claim 1, wherein said hydrotalcite is capable of reversible exfoliation.

9. The synthetic hydrotalcite of claim 1, wherein said divalent cation, $M^{2+}$ comprises $Mg^{2+}$ and up to 50% of at least one divalent cation selected from $Ni^{2+}$, $Co^{2+}$, $Zn^{2+}$, $Cu^{2+}$ and $Mn^{2+}$.

10. The synthetic hydrotalcite of claim 1, wherein said trivalent cation, $M^{3+}$ comprises a mixture of $Al^{3+}$ and up to 50% of at least one trivalent cation selected from $Cr^{3+}$ and $Fe^{3+}$.

11. A synthetic hydrotalcite-poly-addition polymer blend comprising:

at least one poly-addition polymer; and a synthetic hydrotalcite of the general formula;

$$[M^{2+}_{1-x}M^{3+}_x(OH)_2]^{x+}[A^{n-}_{x/n} \cdot mH_2O]^{x-}$$

wherein $M^{2+}$ is a divalent cation, $M^{3+}$ is a trivalent cation and $A^{n-}$ is at least one organic anion comprising a carboxylate of an amino-acid.

12. The synthetic hydrotalcite-poly-addition polymer blend of claim 11, wherein said divalent cation, $M^{2+}$ consists essentially of $Mg^{2+}$.

13. The synthetic hydrotalcite-poly-addition polymer blend of claim 11, wherein said trivalent cation, $M^{3+}$ consists essentially of $Al^{3+}$.

14. The synthetic hydrotalcite-poly-addition polymer blend of claim 11, wherein said at least one poly-addition polymer is selected from the group consisting of polypropylene, polyethylene, polybutene-1, poly-4-methyl pentene-1, polyvinyl chloride and polystyrene.

15. The synthetic hydrotalcite-poly-addition polymer blend of claim 11, wherein said at least one poly-addition polymer comprises a maleated polyolefin.

16. The synthetic hydrotalcite-poly-addition polymer blend of claim 15, wherein said maleated polyolefin comprises maleated polypropylene.

17. The synthetic hydrotalcite-poly-addition polymer blend of claim 11, wherein said amino acid comprises 4-aminobtyric acid.

18. The synthetic hydrotalcite-poly-addition polymer blend of claim 11, wherein said amino acid comprises 6-aminocaproic acid.

19. The synthetic hydrotalcite-poly-addition polymer blend of claim 11, wherein said at least one polymer comprises a maleated polyolefin.

20. The synthetic hydrotalcite-poly-addition polymer blend of claim 19, wherein said maleated polyolefin bonds with said amino acid in the form of an amide.

21. The synthetic hydrotalcite-poly-addition polymer blend of claim 19, wherein said maleated polyolefin bonds with said amino acid in the form of an imide.

22. The synthetic hydrotalcite-poly-addition polymer blend of claim 11, wherein said hydrotalcite is capable of self exfoliation.

23. The synthetic hydrotalcite-poly-addition polymer blend of claim 22, wherein said hydrotalcite is capable of reversible exfoliation.

24. The synthetic hydrotalcite-poly-addition polymer blend of claim 11, wherein said hydrotalcite is capable of reversible exfoliation.

25. The synthetic hydrotalcite-poly-addition polymer blend of claim 11, wherein said divalent cation, $M^{2+}$ contains $Mg^{2+}$ and up to 50% of at least one divalent cation selected from $Ni^{2+}$, $Co^{2+}$, $Zn^{2+}$, $Cu^{2+}$ and $Mn^{2+}$.

26. The synthetic hydrotalcite-poly-addition polymer blend of claim 11, wherein said trivalent cation, $M^{3+}$ contains $Al^{3+-}$ and up to 50% of at least one trivalent cation selected from $Cr^{3+}$ and $Fe^{3+}$.

* * * * *